United States Patent
Saitoh et al.

(10) Patent No.: US 10,827,947 B2
(45) Date of Patent: Nov. 10, 2020

(54) MAGNETIC RESONANCE IMAGING APPARATUS

(71) Applicant: HITACHI, LTD., Tokyo (JP)

(72) Inventors: Yu Saitoh, Tokyo (JP); Satoshi Yamashita, Tokyo (JP)

(73) Assignee: HITACHI, LTD., Tokyo (JP)

(*) Notice: Subject to any disclaimer, the term of this patent is extended or adjusted under 35 U.S.C. 154(b) by 1172 days.

(21) Appl. No.: 15/032,390

(22) PCT Filed: Oct. 23, 2014

(86) PCT No.: PCT/JP2014/078185
§ 371 (c)(1),
(2) Date: Apr. 27, 2016

(87) PCT Pub. No.: WO2015/076054
PCT Pub. Date: May 28, 2015

(65) Prior Publication Data
US 2016/0270690 A1    Sep. 22, 2016

(30) Foreign Application Priority Data
Nov. 19, 2013 (JP) .................... 2013-238844

(51) Int. Cl.
*A61B 5/055* (2006.01)
*G01R 33/38* (2006.01)
(Continued)

(52) U.S. Cl.
CPC ............ *A61B 5/0555* (2013.01); *A61B 5/704* (2013.01); *G01R 33/3802* (2013.01); *G01R 33/3854* (2013.01)

(58) Field of Classification Search
CPC .. A61B 5/704; A61B 5/0555; G01R 33/3802; G01R 33/3854
See application file for complete search history.

(56) References Cited

U.S. PATENT DOCUMENTS

| | | | | |
|---|---|---|---|---|
| 4,849,727 A | * | 7/1989 | Sasaki | ................. G01R 33/421 335/301 |
| 2004/0174167 A1 | * | 9/2004 | Kitagawa | ........... G01R 33/3806 324/318 |

(Continued)

FOREIGN PATENT DOCUMENTS

| JP | 63-143042 | | 6/1988 |
|---|---|---|---|
| JP | S 63143042 A | * | 6/1988 |

(Continued)

OTHER PUBLICATIONS

International Search Report in PCT/JP2014/078185.

*Primary Examiner* — Boniface N Nganga
(74) *Attorney, Agent, or Firm* — Cooper & Dunham LLP

(57) ABSTRACT

A magnetic resonance imaging apparatus according to the invention includes a magnet device that generates a static magnetic field and a gradient magnetic field in an imaging space, a top plate that is provided to freely travel on a bed and sends an object lying thereon into the imaging space, a top plate reception member that is disposed inside the imaging space and has a traveling surface of the top plate, a top plate support column that supports the top plate reception member, and a top plate support pedestal that supports a lower end of the top plate support column, in which the top plate support pedestal is provided on a floor surface on which the magnet device is provided, via a magnet support leg, and is provided so that a movement in a direction along at least the floor surface is restricted to the magnet support leg.

10 Claims, 11 Drawing Sheets

(51) Int. Cl.
*G01R 33/385* (2006.01)
*A61B 5/00* (2006.01)

(56) References Cited

U.S. PATENT DOCUMENTS

| | | |
|---|---|---|
| 2005/0020906 A1 | 1/2005 | Seijger et al. |
| 2008/0015430 A1 | 1/2008 | Takamori |
| 2010/0172468 A1* | 7/2010 | Gregerson ........... A61B 5/0555 378/20 |

FOREIGN PATENT DOCUMENTS

| | | |
|---|---|---|
| JP | 2003-204950 | 7/2003 |
| JP | 2005-508692 | 4/2005 |
| JP | 2008-36400 | 2/2008 |
| JP | 2010-284233 | 12/2010 |
| JP | 201028433 A * | 12/2010 |

* cited by examiner

FIG.10
(a)
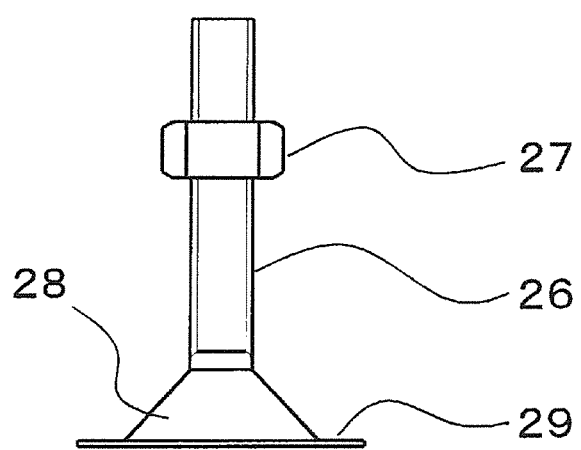
(b)
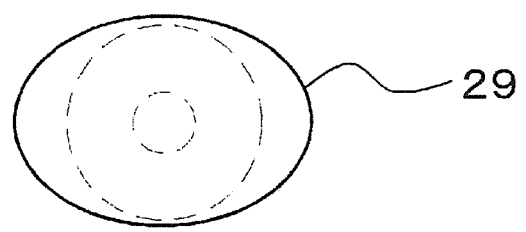

MAGNETIC RESONANCE IMAGING APPARATUS

TECHNICAL FIELD

The present invention relates to a magnetic resonance imaging apparatus, and particularly to a support structure for a top plate which sends an object lying on a bed into an imaging space.

BACKGROUND ART

A magnetic resonance imaging apparatus includes a static magnetic field generation device such as a superconducting magnet which generates a uniform magnetic field in an imaging space; a gradient magnetic field generation device which generates a pulse-like gradient magnetic field in the imaging space in order to add position information to an imaging section; an irradiation coil which generates a high frequency electromagnetic wave causing magnetic resonance in an atomic nucleus forming an object; a reception coil which detects an echo signal (magnetic resonance signal) generated by the magnetic resonance; and the like, and reconfigures an image by using the echo signal so as to obtain a tomographic image.

In such a magnetic resonance imaging apparatus, the gradient magnetic field generation device vibrates due to an interaction between the static magnetic field and a current for driving the gradient magnetic field, and thus a magnet device including the static magnetic field generation device or the like supporting the gradient magnetic field generation device vibrates. On the other hand, the object inserted into the imaging space lies on a top plate which is provided to freely travel on the bed, and is sent into the imaging space. The top plate is mounted to freely travel on a top plate reception member disposed in the imaging space. The top plate reception member is supported at the magnet device or is supported at a floor via a top plate support column so as to be provided. The top plate, the top plate support column, and the like may vibrate due to vibration in the gradient magnetic field generation device. If the top plate vibrates due to vibration in the magnet device or vibration in the gradient magnetic field generation device, the object feels discomfort, and an adverse effect is caused, such as the occurrence of an artifact in a captured image.

Therefore, in the related art, in order to minimize vibration in the top plate, as disclosed in PTL 1 and PTL 2, the top plate, the top plate reception member, and the top plate support column are provided so as not to be in contact with the magnet device in a noncontact manner, and thus transmission of vibration is blocked. A technique has been proposed in which the top plate, the top plate reception member, and the top plate support column are made of non-magnetic materials, and thus a Lorentz force is reduced. For example, in PTL 1, a magnet device including a static magnetic field generation device and a gradient magnetic field device is supported from a floor, and a top plate reception member, a top plate support column, and the like are supported from the floor or a ceiling separately from the magnet device, so that vibration is blocked. On the other hand, PTL 2 has proposed a technique in which a top plate, a top plate reception member, a top plate support column, and the like are made of nonconductive materials, and the top plate support column or the like is floated from a floor surface by air pressure and is supported.

CITATION LIST

Patent Literature

PTL 1: JP-A-10-118043
PTL 2: JP-A-2010-284233

SUMMARY OF INVENTION

Technical Problem

Meanwhile, a vibration frequency has a wide bandwidth, but vibration at which an object frequently feels discomfort is low frequency vibration in an audible frequency range. If the top plate support column supporting the top plate reception member is fixed to a floor, most of the vibration can be attenuated. On the other hand, in order to accurately specify a position of an object relative to the center of the imaging space, a top plate reception portion which is a travel surface of the top plate is required to be accurately provided at a predefined position relative to the magnetic resonance imaging apparatus. Thus, it is necessary to fix a position of the top plate support column or the like to the floor with high accuracy.

However, in order to fix the top plate support column or the like to the floor, work is required, such as burying anchor bolts in a floor surface, or hammering hole-in anchors into the floor. The work of burying the anchor bolts or the like in the floor surface has a problem in that it is hard to ensure position accuracy of the anchor bolt. In other words, position accuracy of the top plate or the top plate reception portion relative to the imaging space which is defined according to a magnetic field device such as the static magnetic field generation device is required to have, for example, about ±0.5 mm. There is a demand for avoiding performing special work of fixing the top plate support column or the like to a floor on a floor surface inside an imaging room in which the magnetic resonance imaging apparatus is installed.

An object of the present invention is to enable a top plate reception portion to be supported from a floor surface without performing special work on the floor surface inside an imaging room, and to secure position accuracy of the top plate reception portion relative to an imaging space.

Solution to Problem

In order to solve the problems, according to the present invention, there is provided a magnetic resonance imaging apparatus including a magnet device that generates a static magnetic field and a gradient magnetic field in an imaging space; a top plate that is provided to freely travel on a bed and sends an object lying thereon into the imaging space; a top plate reception member that is disposed inside the imaging space and has a traveling surface of the top plate; a top plate support column that supports the top plate reception member; and a top plate support pedestal that supports a lower end of the top plate support column, in which the top plate support pedestal is provided on a floor surface on which the magnet device is provided, via a magnet support leg, and is provided by being restricted to the magnet support leg so as to enable a movement in a direction along at least the floor surface.

Advantageous Effects of Invention

According to the present invention, it is possible to support a top plate reception portion from a floor surface without performing special work on the floor surface inside an imaging room, and to secure position accuracy of the top plate reception portion relative to an imaging space.

BRIEF DESCRIPTION OF DRAWINGS

FIG. 10 is a detailed diagram of a subsidiary support leg in Example 2.

DESCRIPTION OF EMBODIMENTS

Hereinafter, a magnetic resonance imaging apparatus of the present invention will be described on the basis of Examples.

Example 1

Figure 1:
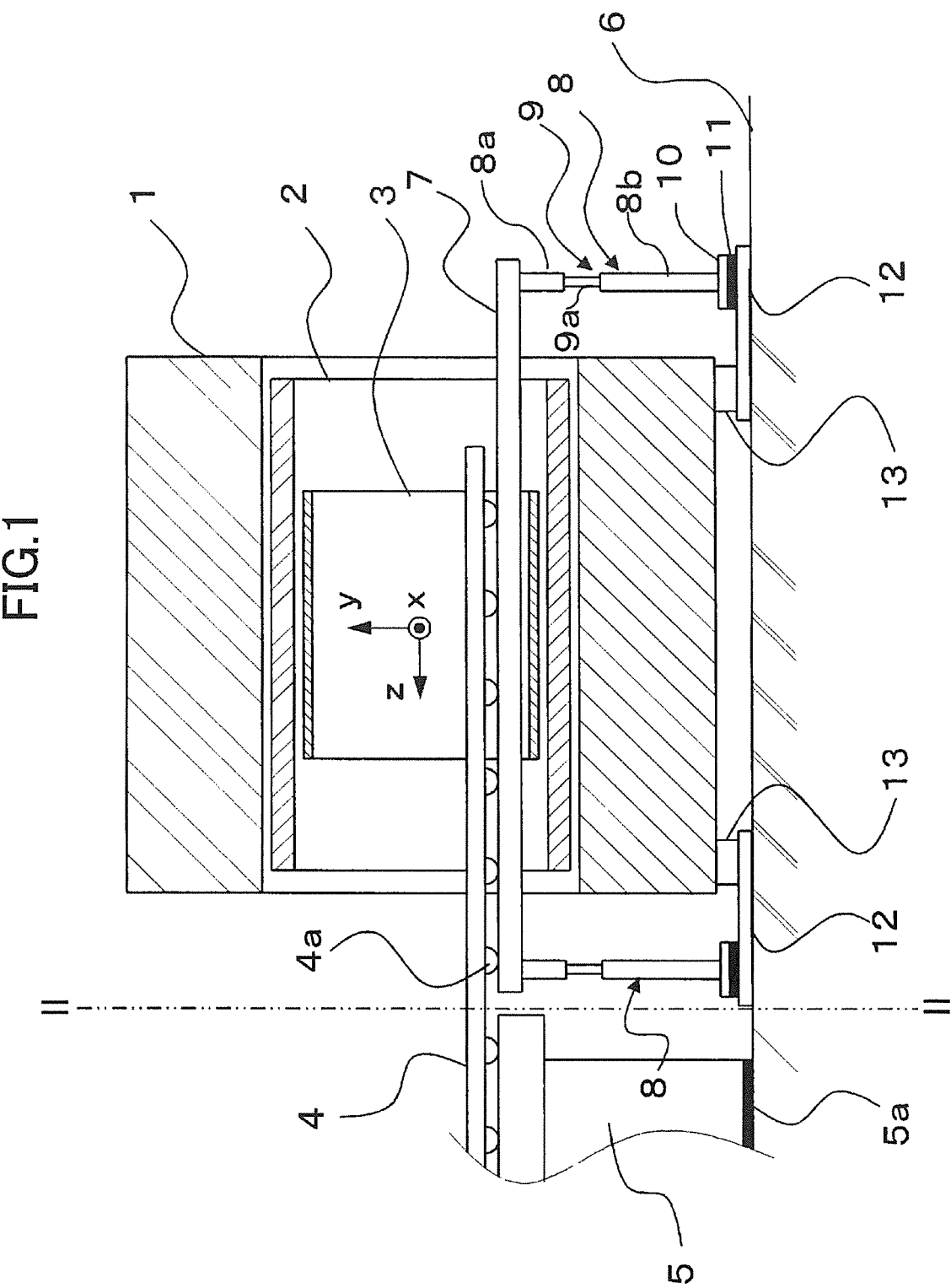
FIG. 1 is a side sectional view of a magnetic resonance imaging apparatus in Example 1 of the present invention.
Figure 2:
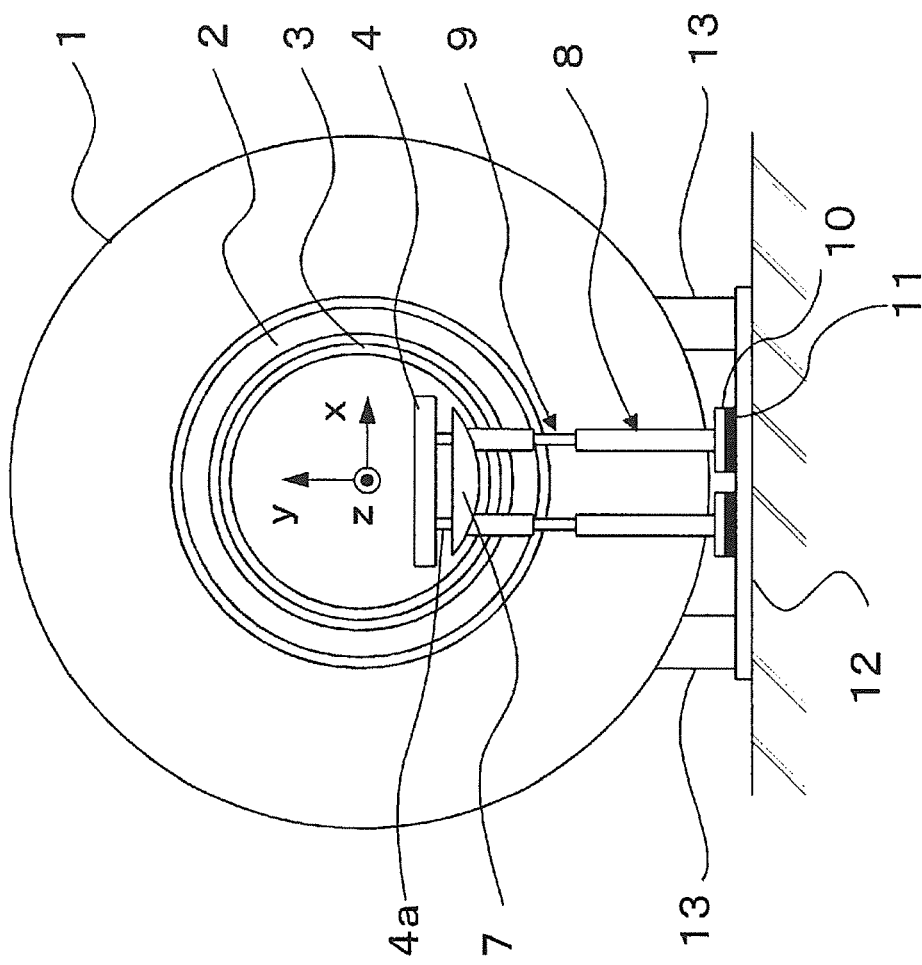
FIG. 2 is a front view of the magnetic resonance imaging apparatus in Example 1.

A magnetic resonance imaging apparatus in Example 1 is configured as a superconducting magnet type horizontal magnetic resonance imaging apparatus as illustrated in FIGS. 1 and 2. However, the present invention is not limited thereto, and is also applicable to a superconducting magnet type vertical magnetic resonance imaging apparatus, or a normal conducting magnet type horizontal or vertical magnetic resonance imaging apparatus.

FIG. 1 is a sectional view in which the magnetic resonance imaging apparatus in Example 1 is cut in a yz plane which is parallel to the paper surface, and FIG. 2 is a front view which is viewed from the line II-II in FIG. 1. Regarding a coordinate system, a vertical direction is indicated as a y axis, a body axis direction is indicated as a z axis, and a direction orthogonal to the y axis and the z axis is indicated as an x axis. The origin is generally taken at the center of an imaging space.

As illustrated in FIGS. 1 and 2, the magnetic resonance imaging apparatus in Example 1 includes a static magnetic field generation device 1 which is formed in a horizontal cylindrical shape, and the imaging space is formed in the cylinder of the static magnetic field generation device 1.

In order to add position information to the imaging space, a cylindrical gradient magnetic field coil 2 constituting a gradient magnetic field device which generates a pulse-like gradient magnetic field having a gradient obtained by inclining spatial magnetic field strength is disposed to surround the imaging space. Although not illustrated, the gradient magnetic field coil is firmly supported at the static magnetic field generation device 1 and is provided on the same axis as that of the cylindrical static magnetic field generation device 1. The static magnetic field generation device 1 and the gradient magnetic field coil 2 constitute a magnet device.

In order to cause nuclear magnetic resonance in an atomic nucleus forming a living body tissue of an object, a cylindrical irradiation coil 3 which irradiates the object with a high frequency signal is supported at the static magnetic field generation device 1 and is disposed on the same axis. The irradiation coil 3 is driven by a signal transmission system (not illustrated). Although not illustrated, a signal reception system including a reception coil or the like detecting an echo signal from the object is provided. As mentioned above, the imaging space is formed in a cylindrical internal space of the irradiation coil 3.

A bed 5 on which a top plate 4 sending the object lying thereon into the imaging space is mounted so as to freely travel is provided to be located at the outside corresponding to the imaging space of the magnet device. The bed 5 is provided on a floor surface 6 via a damping material 5a. A top plate reception member 7 having a traveling surface of the top plate 4 is disposed in the imaging space on an extension line of the bed 5. A plurality of wheels 4a are provided on a lower surface of the top plate 4, and thus the top plate 4 can smoothly travel on the traveling surface of the top plate reception member 7 in the body axis direction (z direction) via the wheels 4a. A position where the top plate 4 is sent can be manually or automatically adjusted. The top plate reception member 7 is provided so that both ends thereof in the longitudinal direction protrude out of both ends of the static magnetic field generation device 1 in the axial direction. Both ends of the top plate reception member 7 are held at predetermined positions via two top plate support columns 8 at each end, that is, four top plate support columns 8 in Example 1.

Here, the top plate support columns 8 supporting the top plate reception member 7 which is a feature portion in Example 1 and related members will be described in detail. In each of the top plate support columns 8, a rectangular flange 10 is provided at a lower end via a column height adjustment portion 9 which adjusts a column height in the vertical direction (y direction), and the flange 10 is mounted on an upper surface of a top plate support pedestal 12 via a damping material 11. Two top plate support pedestals 12 are provided to correspond to the positions of both ends of the top plate reception member 7. The top plate support column 8 is divided into an upper support column 8a and a lower support column 8b. The upper support column 8a and the lower support column 8b are provided with screw holes which are cut into mutually inverse screws at opposing ends, and a screw rod 9a is screwed into the screw holes. The screw rod 9a constitutes the column height adjustment portion 9 which adjusts a height of the top plate support column 8 through rotation thereof. By adjusting a height of the top plate support column 8, a height of the top plate reception member 7, and further a height of the top plate 4 can be adjusted.

The respective top plate support pedestals 12 are formed in the same plate shape, and are mounted on the floor surface 6 so as to correspond to the positions of both ends of the top plate reception member 7. Lower ends of magnet support legs 13 supporting the magnet device including the static magnetic field generation device 1 are mounted on upper surfaces of the top plate support pedestals 12. In Example 1, two magnet support legs 13 are provided at each of lower portions at both ends of the cylindrical static magnetic field generation device 1, and sections of the magnet support legs 13 including lower ends are formed in a rectangular shape. Four magnet support legs 13 are formed to support a total weight (for example, several tons) of the magnet device including the static magnetic field generation device 1 on the floor surface 6 inside the imaging room. However, needless to say, the number of magnet support legs 13 and a sectional shape thereof may be arbitrarily set.

Figure 3:
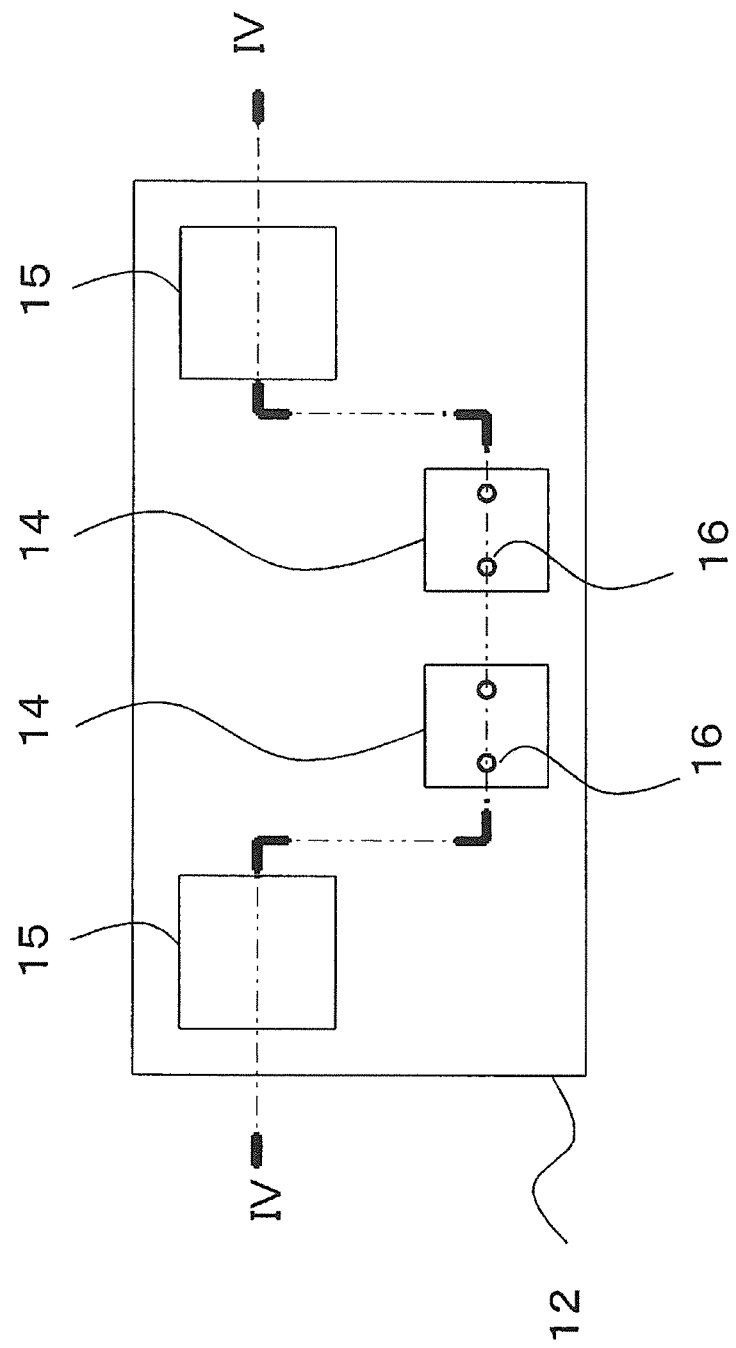
FIG. 3 is a plan view of a top plate support pedestal in Example 1.
Figure 4:
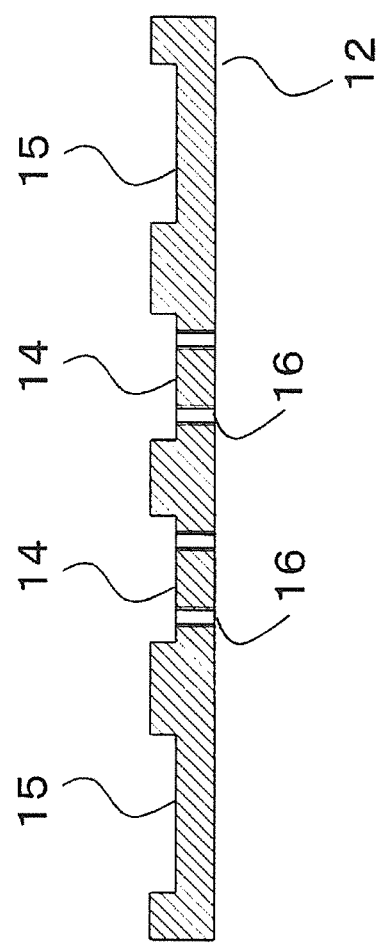
FIG. 4 is a sectional view taken along the line IV-IV in FIG. 3 of the top plate support pedestal in Example 1.

With reference to FIGS. 3 and 4, a configuration of the top plate support pedestal 12 will be described in detail. FIG. 3 is a plan view in which one top plate support pedestal 12 is viewed from the top. As illustrated, the top plate support pedestal 12 is formed in a rectangular shape which is long in the x axis direction of FIG. 1, and is provided with recesses 14 in which the flanges 10 at the lower ends of the top plate support columns 8 are accommodated, and recesses 15 in which the lower end portions of the magnet support legs 13 are accommodated. The two top plate support pedestals 12 are disposed so that the recesses 14 and the recesses 15 are symmetric to each other with the magnet device interposed therebetween. A plurality of (two in the illustrated example) screw holes 16 are formed on a bottom of each of the recesses 14. FIG. 4 is a sectional view taken along the line IV-IV in FIG. 3. Each of the recesses 14 is formed in a rectangular shape so that the rectangular flange 10 of the top plate support column 8 can be fitted thereinto, and each of the recesses 15 is formed in a rectangular shape so that the lower end of the magnet support leg 13 can be fitted thereinto. A depth of each of the recesses 14 and the recesses 15 may be set as appropriate.

Figure 5:
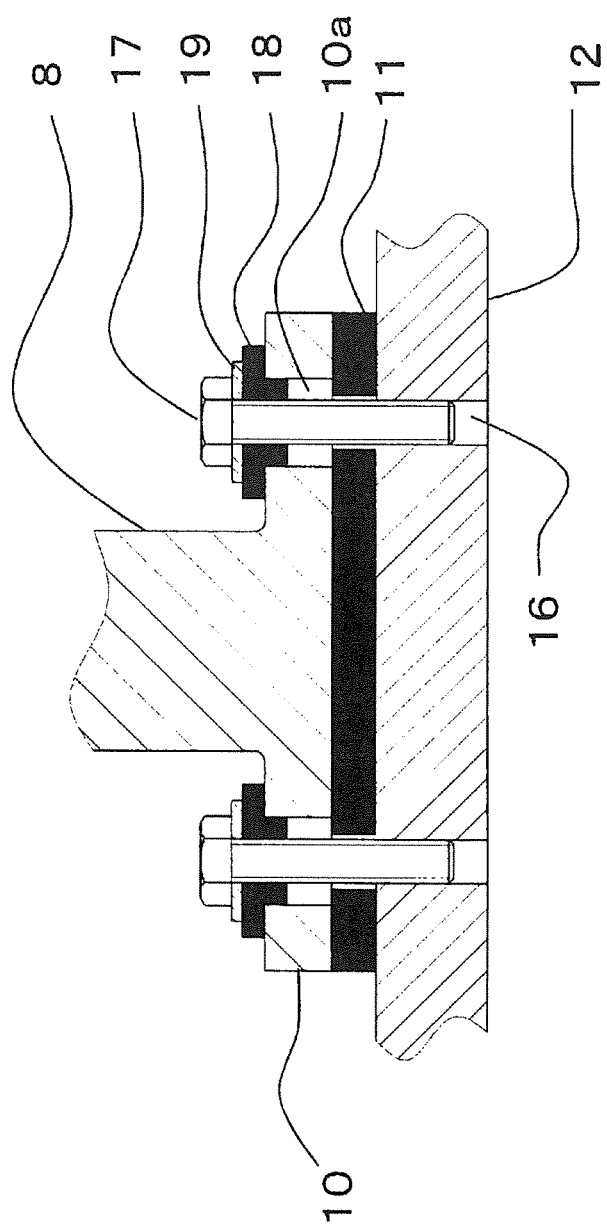
FIG. 5 is a sectional view of a fixation portion which fixes a top plate support column to the top plate support pedestal in Example 1.

As illustrated in FIG. 5, the flange 10 of the top plate support column 8 is fitted into the bottom of the recess 14 of the top plate support pedestal 12 via the damping material 11, and bolts 17 are inserted into penetration holes 10a formed in the flange 10 and are screwed into the screw holes 16. In this case, an elastic washer 18 which is elastic and a metal washer 19 are interposed between the head of the bolt 17 and the flange 10, and the top plate support column 8 is firmly fixed to the top plate support pedestal 12 via the bolt 17. As mentioned above, by using the elastic washer 18 made of rubber, it is possible to block or attenuate vibration which is transmitted from the top plate support pedestal 12 to the top plate support column 8 via the flange 10. The bolt 17 and the metal washer 19 are preferably made of non-magnetic metal such as stainless steel or brass in consideration of being used in a magnetic field. On the other hand, the lower end of the magnet support leg 13 is provided to be fitted into the recess 15. Consequently, in Example 1, a whole weight of the magnet device including the static magnetic field generation device 1 is applied to the top plate support pedestal 12.

As described above, according to Example 1, the top plate support pedestals 12 supporting the top plate reception member 7 are mounted on the floor surface 6 of the imaging room, and the magnet support legs 13 of the magnet device including the static magnetic field generation device 1 are mounted on the upper surfaces of the top plate support pedestals 12. Therefore, the top plate support pedestals 12 are pressed against the floor surface 6 by the weight of the magnet device. Consequently, the top plate support pedestals 12 are firmly fixed to the floor surface 6. The flanges 10 at the lower ends of the top plate support columns 8 are fitted into the recesses 14 formed on the upper surfaces of the top plate support pedestals 12 so as to be mounted on the top plate support pedestals 12, and thus it is possible to maintain relative position accuracy of the top plate 4 supported at the top plate reception member 7 and the imaging space to be high. In other words, the magnet device including the static magnetic field generation device 1 is a heavy weight (for example, several tons), and thus a load applied to the top plate support pedestals 12 in Example 1 is also considerable. Thus, the top plate support pedestals 12 do not move in the vertical direction (y direction) during driving of the magnetic resonance imaging apparatus.

Particularly, in Example 1, since the lower end portions of the magnet support legs 13 are fitted into the recesses 15 of the top plate support pedestals 12, it is possible to prevent the top plate support pedestals 12 from moving in the horizontal direction (the x direction and the z direction). Therefore, it is possible to prevent changes in relative positions between the magnet device including the static magnetic field generation device 1 and the top plate support pedestals 12, and relative positions between the imaging space of the magnet device and the top plate 4. As a result, it is possible to support the top plate 4 and the top plate reception member 7 at the floor surface 6 without performing special work such as burying anchor bolts in the floor surface inside the imaging room, and also to easily ensure position accuracy of the top plate reception member 7 relative to the imaging space.

According to Example 1, in a case where a section of the lower end portion of the magnet support leg 13 is rectangular, corresponding to this section, a section of the recess 15 of the top plate support pedestal 12 is made rectangular, and the lower end portion of the magnet support leg 13 is fitted into the recess 15. Consequently, it is possible to prevent the top plate support pedestals 12 from horizontally rotating about the magnet support legs 13. As a result, it is possible to ensure more easily position accuracy of the top plate reception member 7 relative to the imaging space. Since a load of the magnet device including the static magnetic field generation device 1 applied to the top plate support pedestals 12 via the magnet support legs 13 is considerable, it is not necessary to provide bolts and screw holes for fixing the magnet support legs 13 to the top plate support pedestals 12.

According to Example 1, since the top plate support columns 8 and the bed 5 are vibration-insulated from the floor surface 6 and the top plate support pedestals 12 by the damping materials 5a and the damping materials 11, it is possible to minimize or attenuate transmission of vibration from the static magnetic field generation device 1 and the gradient magnetic field coil 2 as vibration generation sources to the top plate reception member 7 and the top plate 4. Consequently, it is possible to reduce vibration in the top plate 4, to thus reduce discomfort which an object feels, and also to reduce mixing of artifact caused by the vibration with an image.

In order to reliably insulate vibration, the damping material 5a and the damping material 11 are preferably provided, but the damping materials may be omitted in a case where it is founded in advance by other means that vibration is sufficiently slight. On the contrary, in a case where there is a concern that vibration in the magnet device including the static magnetic field generation device 1 may be transmitted to the floor surface 6 and the top plate support pedestals 12, damping materials may also be provided between the magnet support legs 13 and the top plate support pedestals 12.

Example 2

With reference to FIGS. 6 to 10, a magnetic resonance imaging apparatus in Example 2 will be described. Differences between Example 2 and Example 1 are a shape of the magnet support leg of the magnet device, a structure and a shape of the top plate support pedestal, a load applying method for the top plate support pedestal, and the like. Hereinafter, a description will be made focusing on the differences from Example 1, and the same constituent elements are given the same reference numerals, and description thereof will not be repeated.

Figure 6:
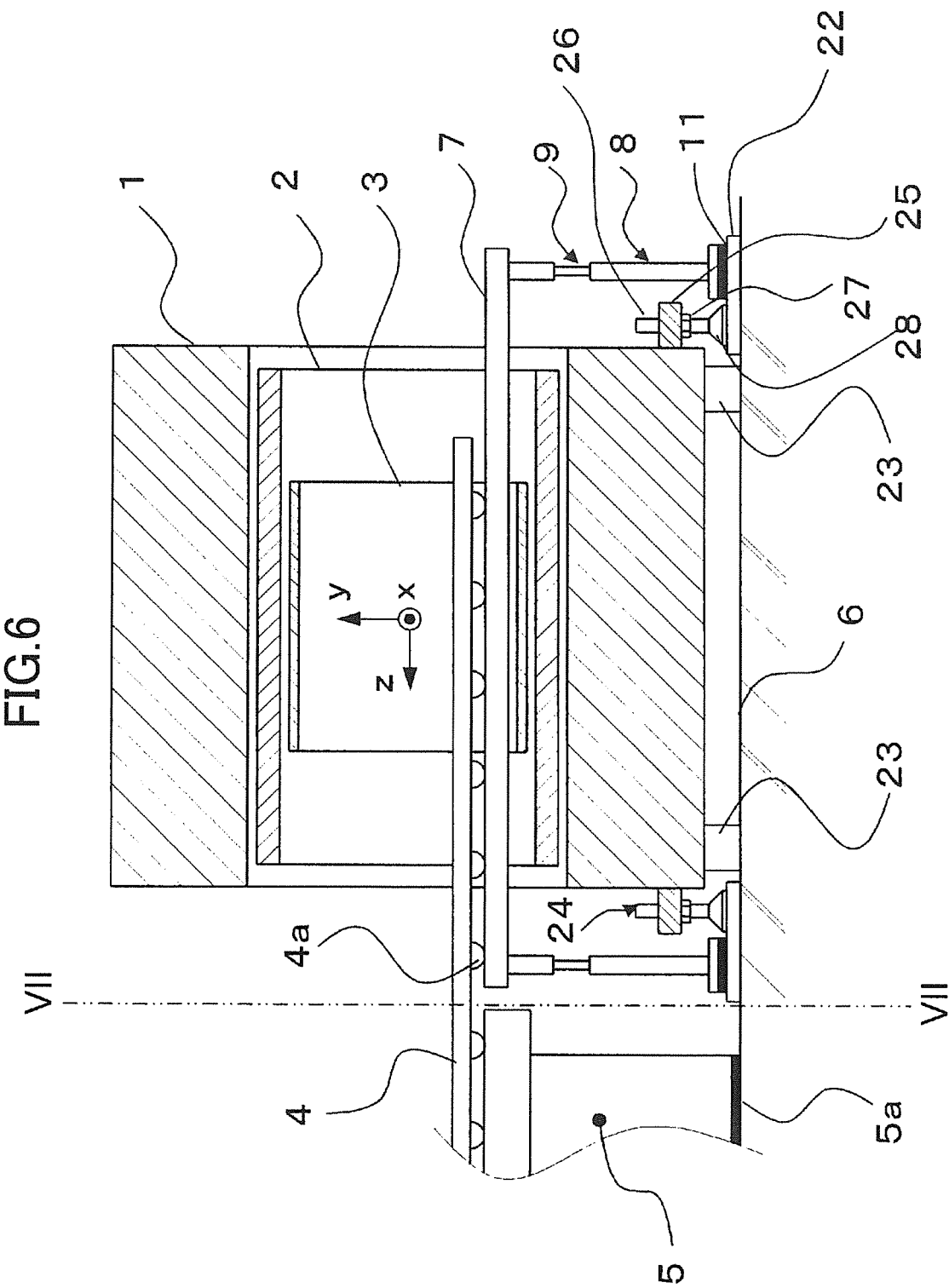
FIG. 6 is a side sectional view of a magnetic resonance imaging apparatus in Example 2 of the present invention.
Figure 7:
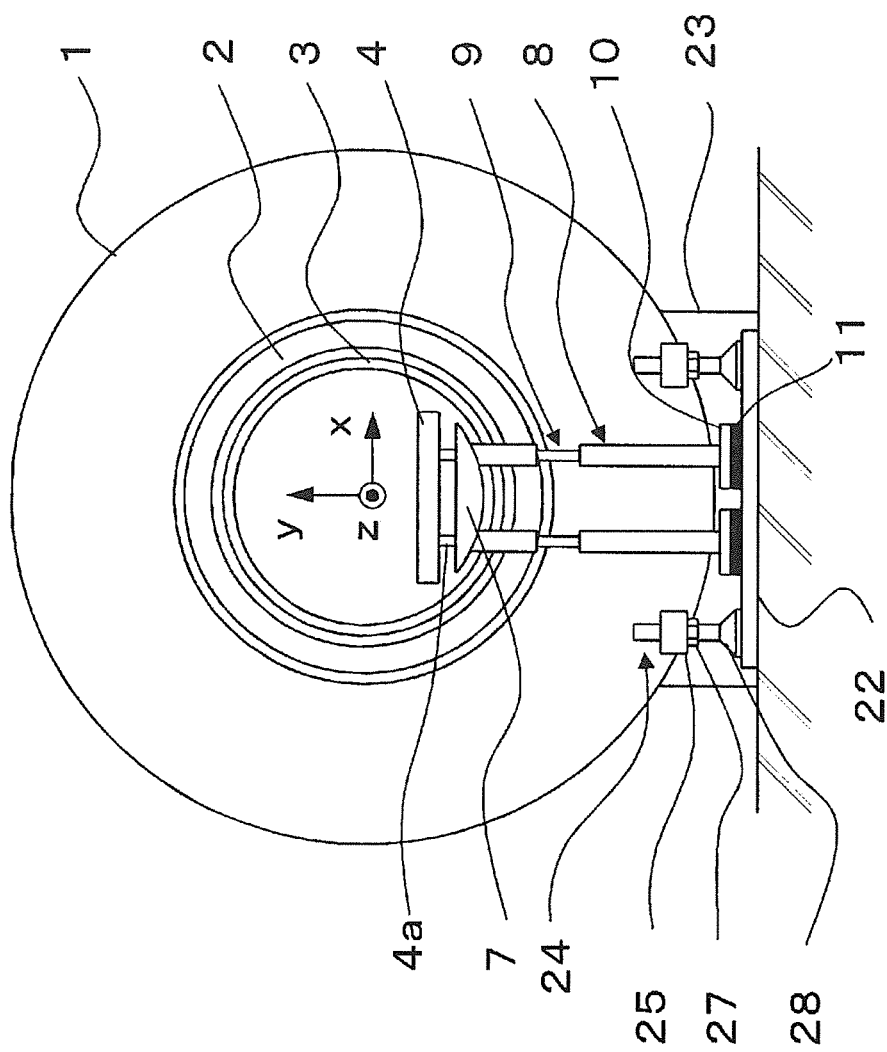
FIG. 7 is a front view of the magnetic resonance imaging apparatus in Example 2.
Figure 8:
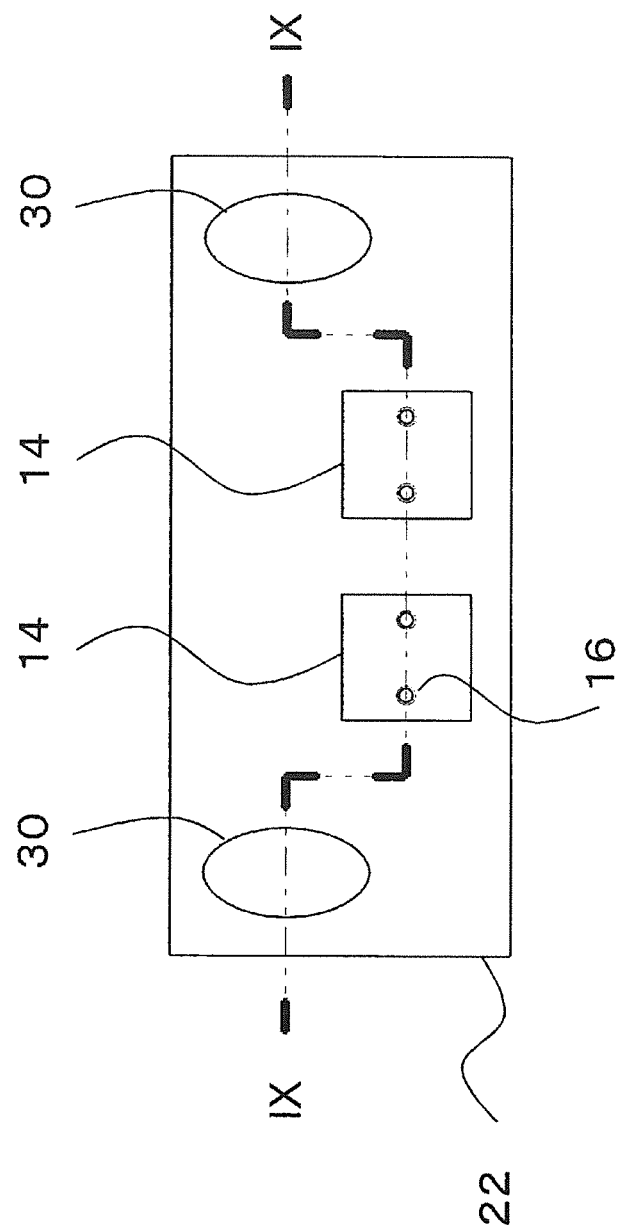
FIG. 8 is a plan view of a top plate support pedestal in Example 2.

As illustrated in FIGS. 6 and 7, magnet support legs 23 supporting the static magnetic field generation device 1 are provided integrally with lower portions at both ends of the static magnetic field generation device 1 and are thus directly mounted on the floor surface 6. Example 2 is characterized in that a pair of subsidiary support legs 24 are fixed and provided at each of cylindrical end surfaces of the static magnetic field generation device 1. Each of the subsidiary support legs 24 includes a subsidiary leg fixation member 25 which is fixed and provided at the cylindrical end surface of the static magnetic field generation device 1, a subsidiary leg rod 26 which is inserted into a penetration hole formed in the subsidiary leg fixation member 25 in the vertical direction (y direction), a nut 27 which is screwed into a male screw formed on an outer circumference of the subsidiary leg rod 26, and a reverse umbrella-shaped leg seat 28 which is provided at a lower end of the subsidiary leg rod 26.

Therefore, in the subsidiary support leg 24, the nut 27 is rotated and is thus moved vertically along the subsidiary leg rod 26. If the nut is further moved up and down along the subsidiary leg rod 26 in a state of being brought into contact with the subsidiary leg fixation member 25, a height of the subsidiary support leg 24 can be adjusted. An elliptical base plate 29 is provided on a lower surface of the leg seat 28 as illustrated in FIG. 10(b).

Figure 9:
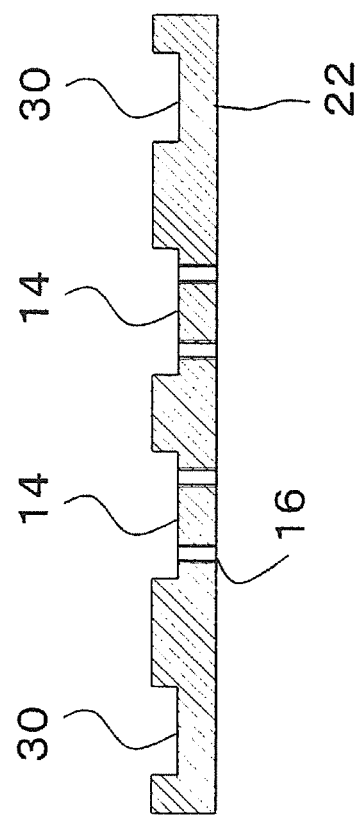
FIG. 9 is a sectional view taken along the line IX-IX in FIG. 8 of the top plate support pedestal in Example 2.

The subsidiary support leg 24 configured as mentioned above is mounted on a top plate support pedestal 22 via the base plate 29 of the leg seat 28. As illustrated in a plan view of FIG. 8, the top plate support pedestal 22 is provided with recesses 30 into which the base plates 29 are fitted. FIG. 9 illustrates a section of the top plate support pedestal 22 cut along the line IX-IX in FIG. 8. A difference between the top plate support pedestal 22 of Example 2 and the top plate support pedestal 12 of Example 1 is that an opening section of the recess 30 into which the base plate 29 of the leg seat 28 is fitted is formed in an elliptical shape in accordance with the exterior of the base plate 29. Consequently, even if a height of the subsidiary support leg 24 is adjusted by rotating the nut 27, it is possible to prevent the base plate 29 from rotating relative to the top plate support pedestal 22. The top plate support columns 8 and the flanges 10 are formed in the same manner as in Example 1, and thus the top plate support columns are mounted on the top plate support pedestals 22 via the flanges 10.

With this configuration, according to Example 2, particularly, even in a state in which the magnet device including the static magnetic field generation device 1 is provided on the floor surface 6, Example 2 is meaningful in that the top plate support pedestals 22 can be provided without moving the static magnetic field generation device 1, compared with Example 1.

According to Example 2, when the nut 27 of the subsidiary support leg 24 becomes distant from the lower surface of the subsidiary leg fixation member 25 in a state of being loosened, the entire weight of the magnet device including the static magnetic field generation device 1 is applied to the floor surface 6. If the nut is rotated, and the nut 27 is further rotated in a direction in which the nut is moved up from a position where the nut is brought into contact with the lower surface of the subsidiary leg fixation member 25, the weight of the magnet device is applied to both of the floor surface 6 and the top plate support pedestal 22. If the nut 27 is still further rotated in the direction in which the nut is moved up, a load applied to the top plate support pedestal 22 increases, and thus a force for fixing the top plate support pedestal 22 to the floor surface 6 increases.

The weight of the magnet device applied to the top plate support pedestals 22 of Example 2 is smaller than the weight in Example 1, but the magnet device including the static magnetic field generation device 1 is a heavy weight. Thus, if the nuts 27 are sufficiently fastened to the subsidiary leg fixation members 25, the top plate support pedestals 22 do not move in the vertical direction (y direction) during driving of the magnetic resonance imaging apparatus.

Since a shape of the opening section of the recess 30 of the top plate support pedestal 22 is made elliptical in accordance with the elliptical shape of the base plate 29 of the leg seat 28 of the subsidiary support leg 24, it is possible to prevent the top plate support pedestals 22 from moving in the horizontal direction (the x direction and the z direction) and also to prevent the top plate support pedestals 22 from rotating in the horizontal direction. When a height of the subsidiary support leg 24 is adjusted by rotating the nut 27, the subsidiary leg rod 26 can be prevented from being rotated together, and thus it is possible to stably adjust a height of the subsidiary support leg 24.

In the same manner as in Example 1, the leg seat 28 of the subsidiary support leg 24 is not required to be fixed to the top plate support pedestal 22 with screws.

Example 3

Figure 11:
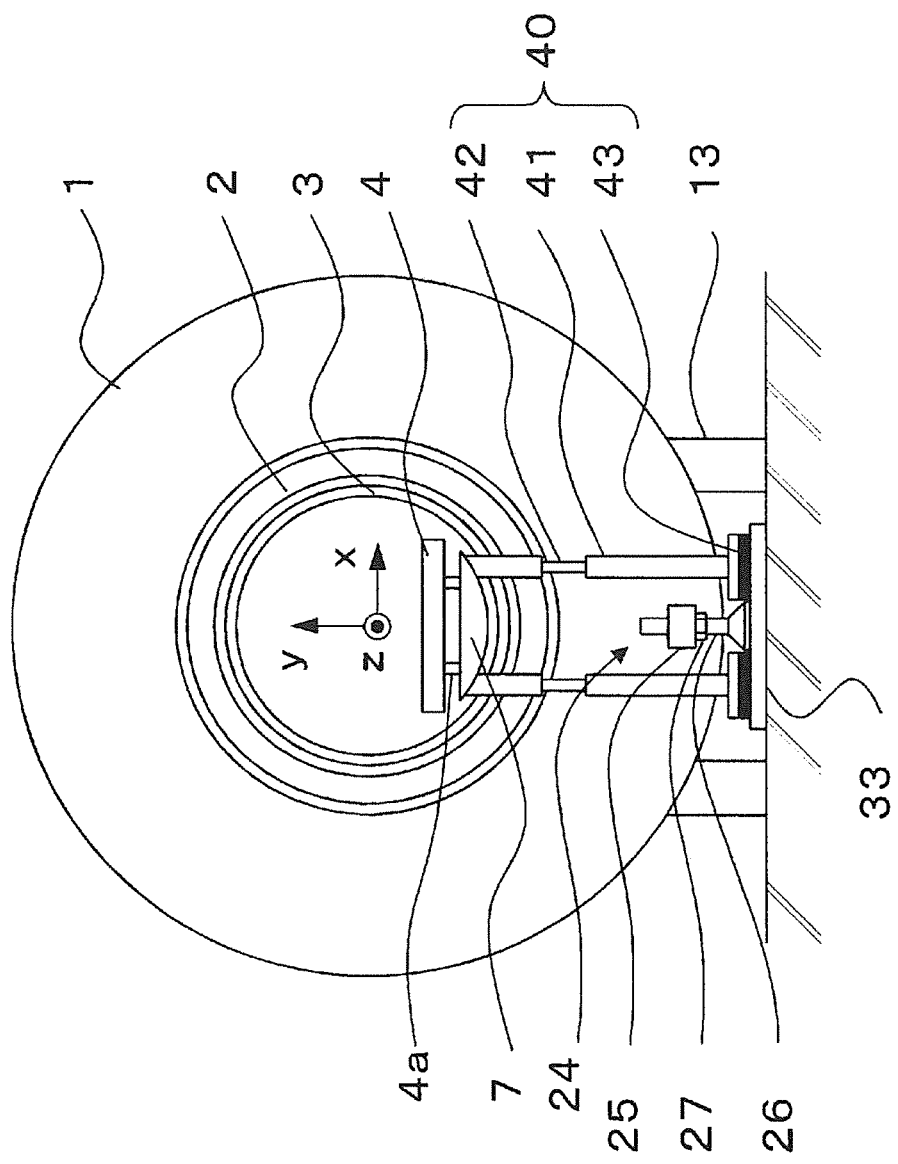
FIG. 11 is a front view of a magnetic resonance imaging apparatus in Example 3.

With reference to FIG. 11, a magnetic resonance imaging apparatus in Example 3 will be described. Differences between Example 3 and Example 2 are a shape of the magnet support leg of the magnet device, a structure and a shape of the top plate support pedestal, a load applying method for the top plate support pedestal, and the like. Hereinafter, a description will be made focusing on the differences from Example 2, and the same constituent elements are given the same reference numerals, and description thereof will not be repeated.

In Example 3, two magnet support legs 13 are provided at each of both cylindrical ends of the static magnetic field generation device 1 and are mounted on the floor surface 6 in the same manner as in Example 1. In Example 3, a single subsidiary support leg 24 is provided at a central portion of a cylindrical end surface of each of both ends of the static magnetic field generation device 1. Others are the same as in Example 2.

In other words, the subsidiary support leg 24 includes a subsidiary leg fixation member 25 which is fixed and provided at the central portion of the cylindrical end surface of the static magnetic field generation device 1, a subsidiary leg rod 26 which is inserted into a penetration hole formed in the subsidiary leg fixation member 25 in the vertical direction (y direction), a nut 27 which is screwed into a male screw formed on an outer circumference of the subsidiary leg rod 26, and a reverse umbrella-shaped leg seat 28 which is provided at a lower end of the subsidiary leg rod 26.

Therefore, in the subsidiary support leg 24, the nut 27 is rotated and is thus moved vertically along the subsidiary leg rod 26. If the nut is further moved up and down along the subsidiary leg rod 26 at a position where the nut is brought into contact with the subsidiary leg fixation member 25, a height of the subsidiary support leg 24 can be adjusted. The elliptical base plate 29 is provided on a lower surface of the leg seat 28 as illustrated in FIG. 10(b).

A top plate support pedestal 33 of Example 3 is formed in the same manner as the top plate support pedestal 22 of Example 2. However, the subsidiary support leg 24 is provided alone, and thus a single recess 30 into which the base plate 29 of the leg seat 28 of the subsidiary support leg 24 is fitted may be provided at a central portion of the top plate support pedestal.

According to Example 3, it is possible to achieve the same effects as in Examples 1 and 2.

As mentioned above, the present invention has been described on the basis of Examples 1 to 3, but the present invention is not limited to such Examples, and the object of the present invention can be achieved even if various modifications are applied thereto. In other words, a magnetic resonance imaging apparatus is configured to include a magnet device that generates a static magnetic field and a gradient magnetic field in an imaging space; a top plate that is provided to freely travel on a bed and sends a object lying thereon into the imaging space; a top plate reception member that is disposed inside the imaging space and has a traveling surface of the top plate; a top plate support column that supports the top plate reception member; and a top plate support pedestal that supports a lower end of the top plate support column. Particularly, the top plate support pedestal may be provided on a floor surface on which the magnet device is provided, via a magnet support leg, and may be provided so that a movement in a direction along at least the floor surface is restricted to the magnet support leg.

As mentioned above, if movement of the top plate support pedestal in the direction along the floor surface is restricted to the magnet support leg, the top plate support pedestal does not move along the floor surface. Specifically, for example, this can be handled by providing an overhanging portion which can be locked to or engaged with the periphery of the magnet support leg on the top plate support pedestal. In addition, an overhanging portion is provided from the magnet support leg toward the top plate support pedestal, and the top plate support pedestal is fixed to the overhanging portion with screws so that the top plate support pedestal can be restricted to the magnet support leg. Also with such a modification example, it is possible to prevent relative positions between the top plate supported at the top plate support pedestal and the imaging space from being deviated in the horizontal direction.

Since the top plate, the top plate reception member, and the top plate support column have some weights, and further an object lies on the top plate, the top plate is hardly positionally deviated in the vertical direction. Therefore, it is possible to sufficiently ensure relative position accuracy of the top plate and the imaging space. If one overhanging portion is formed so that the overhanging portion locks the top plate support pedestal and the magnet support leg to each other in order to restrict vertical movement, floating of the top plate support pedestal and further the top plate, that is, movement in the direction vertical to the floor surface can be restricted to the magnet support leg and can thus be prevented.

In Examples 1 to 3, a plurality of recesses are formed on the upper surface of the top plate support pedestal, and the lower end portion of the magnet support leg and the lower end portion of the top plate support column are fitted into the recesses, but a configuration in which the magnet support leg is only mounted on the upper surface of the top plate support pedestal may be employed without forming the recesses. In a case of the top plate support column is not fitted into the recess, the lower end portion thereof is preferably fixed to the top plate support pedestal with screws.

A shape of the recess on the upper surface of the top plate support pedestal described in Examples 1 to 3 is not limited to a rectangular shape or an elliptical shape, and may employ a circular shape, a quadrangle shape, and a polygonal shape in accordance with shapes of the lower end portion of the magnet support leg and the lower end portion of the top plate support column.

A description has been made of an example in which the top plate support pedestal described in Examples 1 to 3 is provided to be in common to the two top plate support columns 8 at both ends of the static magnetic field generation device 1 in the axial direction, but may be separately provided to correspond to each of the top plate support columns 8.

As mentioned above, the present invention has been described on the basis of one embodiment, but the present invention is not limited thereto, and it is obvious to a person skilled in the art that the present invention can be implemented in a modified or altered form within the scope thereof. In addition, such a modified or altered form is naturally included in the claims of the present application.

REFERENCE SIGNS LIST

1 STATIC MAGNETIC FIELD GENERATION DEVICE, 2 GRADIENT MAGNETIC FIELD COIL, 3 IRRADIATION COIL, 4 TOP PLATE, 4a WHEEL, 5 BED, 6 FLOOR SURFACE, 7 TOP PLATE RECEPTION MEMBER, 8 TOP PLATE SUPPORT COLUMN, 9 COLUMN HEIGHT ADJUSTMENT PORTION, 10 FLANGE, 11 DAMPING MATERIAL, 12 TOP PLATE SUPPORT PEDESTAL, 14, 15, 30 RECESS, 18 ELASTIC WASHER, 22 TOP PLATE SUPPORT PEDESTAL, 19 METAL WASHER, 24 SUBSIDIARY SUPPORT LEG, 25 SUBSIDIARY LEG FIXATION MEMBER, 26 SUBSIDIARY LEG ROD, 27 NUT, 28 LEG SEAT, 29 BASE PLATE

The invention claimed is:

1. A magnetic resonance imaging apparatus comprising:
    a magnet device that generates a static magnetic field and a gradient magnetic field in an imaging space;
    a top plate that is provided to freely travel on a bed and sends an object lying thereon into the imaging space;
    a top plate reception member that is disposed inside the imaging space and has a traveling surface of the top plate;
    a top plate support column that supports the top plate reception member;
    a top plate support pedestal that supports a lower end of the top plate support column and is provided on a floor surface; and
    a magnet support leg that supports the magnet device and is mounted on an upper surface of the top plate support pedestal.

2. The magnetic resonance imaging apparatus according to claim 1, wherein the magnet support leg restricts a movement of the top plate support pedestal in a direction vertical to the floor surface.

3. The magnetic resonance imaging apparatus according to claim 1, wherein the top plate support pedestal is provided with a recess that accommodates a lower end portion of the top plate support column.

4. The magnetic resonance imaging apparatus according to claim 3, wherein an additional recess that accommodates a lower end portion of the magnet support leg is disposed in the upper surface of the top plate support pedestal on which said magnet support leg is mounted.

5. The magnetic resonance imaging apparatus according to claim 4, wherein an opening of the additional recess into which the lower end portion of the magnet support leg is inserted is formed in accordance with a sectional shape of the lower end portion.

6. The magnetic resonance imaging apparatus according to claim 1, wherein the magnet support leg is fixed without a bolt.

7. The magnetic resonance imaging apparatus according to claim 1, wherein the top plate support pedestal is provided with a screw hole to which a flange formed at a lower end portion of the top plate support column is fixed with a bolt.

8. The magnetic resonance imaging apparatus according to claim 7, wherein the flange is fixed to the top plate support pedestal with a bolt via a damping material, and a damping washer is interposed between a bolt head and the flange.

9. The magnetic resonance imaging apparatus according to claim 1, further comprising a subsidiary support leg disposed to support a load of a part of the magnet device and mounted on an upper surface of the top plate support pedestal.

10. The magnetic resonance imaging apparatus according to claim 9, wherein the subsidiary support leg is disposed to permit adjustment of a height of said subsidiary support leg.

* * * * *